US00PP25495P2

(12) United States Plant Patent
Delabroye

(10) Patent No.: US PP25,495 P2
(45) Date of Patent: Apr. 28, 2015

(54) ***HEUCHERA* PLANT NAMED 'CIRCUS'**

(50) Latin Name: ***Heuchera* hybrid**
Varietal Denomination: Circus

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 182 days.

(21) Appl. No.: 13/694,450

(22) Filed: Dec. 4, 2012

(51) Int. Cl.
*A01H 5/00* (2006.01)

(52) U.S. Cl.
USPC ..... Plt./440

(58) Field of Classification Search
CPC ..... A01H 5/02; A01H 5/025; A01H 5/00; A01H 5/12
USPC ..... Plt./440
See application file for complete search history.

(56) References Cited

PUBLICATIONS

Rice. *Heuchera* 'Circus': Plant of the Year finalist, posted on Jun. 11, 2012, retrieved on Jul. 29, 2014, retrieved from the Internet at <http://mygarden.rhs.org.uk/blogs/graham_rice/archive/2012/06.aspx> 4 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Circus', characterized by its foliage with leaves that are peach colored with reddish veining in spring and fall and lime green with a slight silver overlay and red veining in summer, its pinkish purple flowers on red flowering stems, its tolerance to heat and humidity, its vigorous growth habit, and its hardiness in U.S.D.A Zones 3 to 8.

2 Drawing Sheets

Botanical classification: *Heuchera* hybrid.
Cultivar designation: 'Circus'.

CROSS REFERENCE TO RELATED APPLICATIONS

This application is co-pending with a U.S. Plant Patent Application filed for a plant derived from the same breeding program that is entitled *Heuchera* Plant Named 'Vulcano' (U.S. Plant patent application Ser. No. 13/694,477), and *Heuchera* Plant Named 'Pretty Perrine' (U.S. Plant patent application Ser. No. 13/694,476).

BACKGROUND OF THE INVENTION

The present invention relates to a new and distinct cultivar of *Heuchera* of hybrid origin, botanically known as a *Heuchera* and is hereinafter referred to by its cultivar name 'Circus'.

The new cultivar was discovered as a whole plant mutation by the Inventor in Hantay, France. The Inventor sowed seeds that were pooled from crosses made between proprietary plants in his breeding program in 2009. The Inventor selected 'Circus' in 2011 as a single unique plant amongst the seedlings that resulted from the above crosses. The exact parentage is unknown, however at least one of the hybrid parents has *Heuchera*×*villosa* in its heritage due to the observed heat and humidity tolerance observed for the new cultivar.

Asexual propagation of the new cultivar was first accomplished by the Inventor by division in Hantay, France in 2011. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Circus' as a new and unique cultivar of *Heuchera*.

1. 'Circus' exhibits uniquely colored foliage with leaves that are peach colored with reddish veining in spring and fall and lime green with a slight silver overlay and red veining in summer.
2. 'Circus' exhibits pinkish purple flowers on red flowering stems.
3. 'Circus' is tolerant to heat and humidity imparted by having *Heuchera*×*villosa* in its parentage.
4. 'Circus' exhibits a vigorous growth habit.
5. 'Circus' is hardy in U.S.D.A. Zones 3 to 8.

'Circus' is a unique *Heuchera* with foliage coloration that is unknown to exist in other cultivars of *Heuchera* known to the Inventor. 'Circus' can be compared most closely to 'Tiramisu' (U.S. Plant Pat. No. 20,429), 'Vulcano', 'Pretty Perrine' and 'Electra' (U.S. Plant Pat. No. 21,856) for its similarity in having foliage that is marked with red and in having *Heuchera*×*villosa* in its parentage. 'Tiramisu' differs from 'Circus' in having yellow-green foliage that is mottled with red between the veins and in lacking red flowering stems. 'Vulcano' differs from 'Circus' in having amber colored foliage with a silver overlay and veins and margins that are light brownish red. 'Pretty Perrine' differs from 'Circus' in having lime green leaves with red mottling in the center of the leaves and in having white flowers. 'Electra' differs from 'Circus' in having spring foliage that is bright yellow-gold with red veins, rather than peach colored.

BRIEF DESCRIPTION OF THE DRAWING

The accompanying colored photographs illustrate the overall appearance and distinct characteristics of the new *Heuchera*. The photographs were taken of a plant two years in age as grown outdoors in a 10-liter container in Hantay, France.

The photograph in FIG. 1 provides a view of the plant habit, changing foliage coloration, and flowering stems of 'Circus'.

Figure 1:
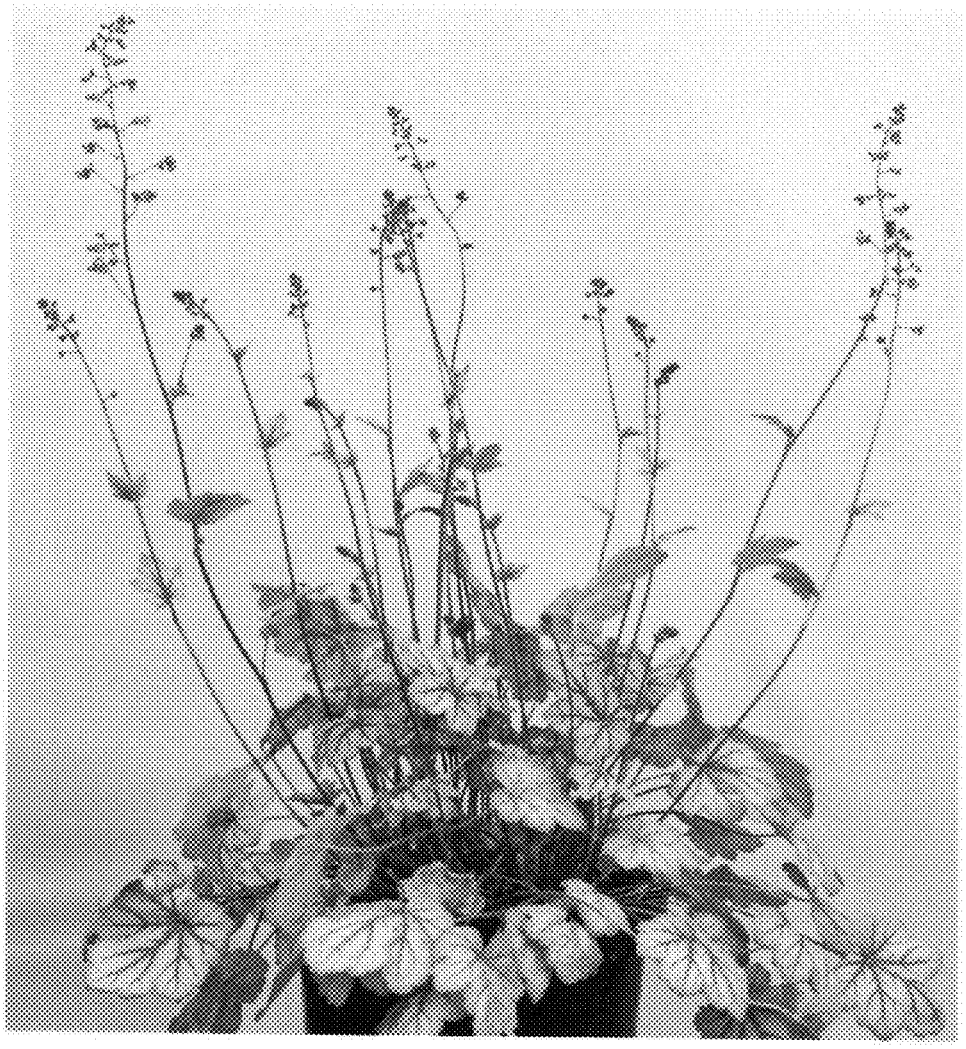
Figure 2:
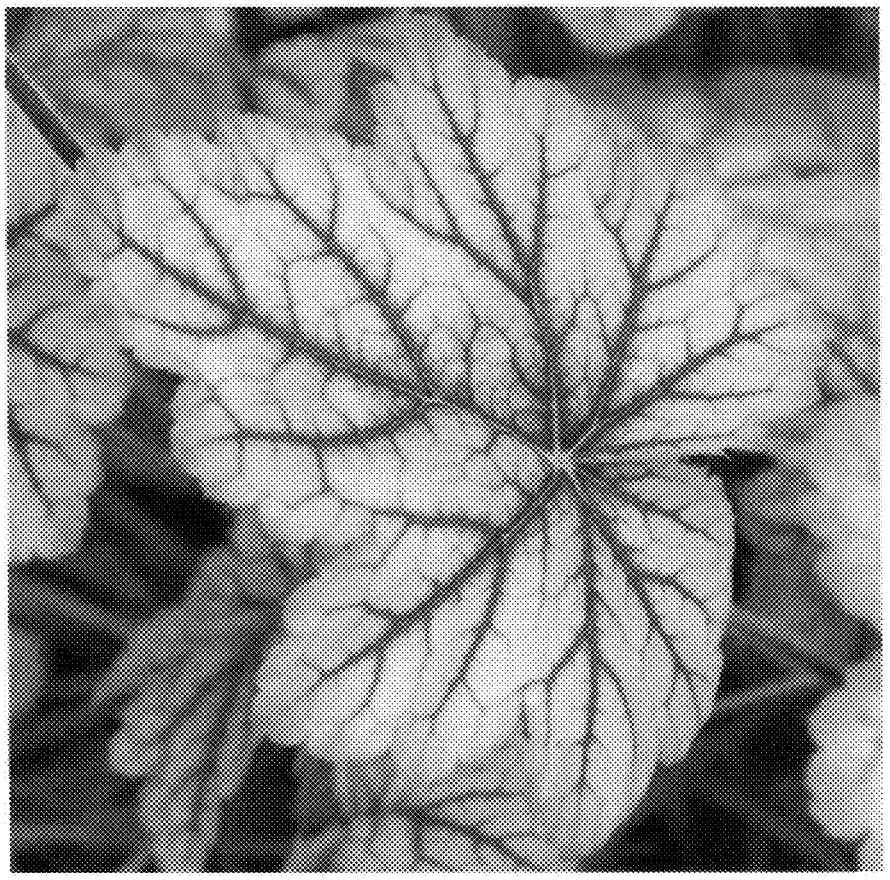

The photograph in FIG. 2 provides a close-up view of a spring leaf of 'Circus'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown outdoors in April in 10-liter containers in Hantay France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—May to July in Hantay, France.

*Plant type.*—Herbaceous perennial.

*Plant habit.*—Compact, clump-forming, mounded foliage.

*Height and spread.*—Average of 31.5 cm in height from soil to top of leaves, 67 cm from soil to top of inflorescences, and about 70 cm in width.

*Hardiness.*—At least in U.S.D.A. Zones 3 to 8.

*Diseases and pests.*—Not more susceptible to pests and diseases than other *Heuchera* varieties.

*Root description.*—Fibrous roots on woody rootstalks.

*Branching habit.*—Basal rosette, no lateral branches.

*Propagation.*—In vitro propagation is the preferred method, division is also possible.

*Growth rate.*—Vigorous.

Stem description:

*Shape.*—Round.

*Stem color.*—183A.

*Stem size.*—An average of 3 mm in diameter and 67 cm in length (including primary peduncle).

*Stem strength.*—Strong.

*Stem aspect.*—Flowering stems grow in an average angle of 65° to base (0°=horizontal).

*Stem surface.*—Moderately glossy, rounded, densely covered with short hairs, an average of 1 mm in length and 156D in color.

*Stem number.*—Average of 30 flowering stems and an average of 2 flowering stems per rosette.

Foliage description:

*Leaf shape.*—Broad ovate.

*Leaf division.*—Simple.

*Leaf base.*—Hastate, slightly overlapping.

*Leaf apex.*—Obtuse.

*Leaf venation.*—Laciniate, upper surface; N144A in center with around center and other veins 177A in summer and 183B in spring and fall, lower surface; a blend of 145A and 145B.

*Leaf margins.*—Lobed with an average of 9 lobes per leaf, lobe margins are crenate.

*Leaf attachment.*—Petiolate.

*Leaf arrangement.*—Alternate, basal rosettes.

*Leaf surface.*—Both surfaces dull and moderately covered with short hairs an average of 0.5 mm in length and 157D in color.

*Leaf color.*—Young upper surface (spring and fall); 18C with margins 150B, area near veins 183B, young lower surface (spring and fall); 151A, area near veins tinged 178A, summer upper surface; between 145B and 150B with an overlay of 196D, area near the veins between 166A and 176B with older leaves between 151D and 154B, area near veins 174A, summer lower surface; N144A, area near the veins 177D.

*Leaf size.*—Average of 10.9 cm in length and 10.2 cm in width, winter foliage upper and lower surface; 162D, typically cut back prior to emergence of spring foliage.

*Leaf quantity.*—7 per basal rosette.

*Petioles.*—Average of 23.8 cm in length and 2 mm in diameter, color; 183A.

*Stipules.*—Small leafy stipules at the base of each leaf, laciniate (fringed) apex, with an average of 1.3 cm in length and 3 mm in width and 186B in color.

Flower description:

*Inflorescence type.*—Numerous small bell-shaped flowers arranged on pyramidal panicles on flower scapes emerging from the base of the rosette.

*Inflorescence size.*—An average of 23.6 cm in height (excluding peduncle) and about 8.4 cm in width.

*Flower fragrance.*—None.

*Flower quantity.*—Average of 20 flowers per stem and 150 flowers per inflorescence.

*Flower lastingness.*—Average of one week.

*Flower buds.*—Obovate in shape, an average of 6 mm in length and 3 mm in diameter, color; 50A, 46A at the tip and 35B at the base.

*Flower aspect.*—Drooping to outward.

*Flower type.*—Campanulate.

*Flower size.*—About 7 mm in depth (height) and 8 mm in diameter.

*Petals.*—Average of 5, rotate arrangement and implanted in the hypanthium at the lower half of the calyx, petals and filaments are fused, obovate in shape, margin is entire, apex is acute, upper and lower surface is dull and smooth, color: upper and lower surface when opening; 65A becoming 65B at the base, upper and lower surface when fully opened; 65B becoming 65C at the base.

*Calyx.*—Campanulate, 7 mm in length and 8 mm in diameter.

*Sepals.*—Campanulate hypanthium, average of 5, fused into hypanthium, elliptic to oblong in shape, about 7 mm in length and 2 mm in width, margin is entire, apex is broadly acute, fused base, color: immature upper surface; 53B, base 53C, immature lower surface; 50A, tip 46A, base 35B, mature upper surface; 53B, base 53C, mature lower surface; 50A, tip 46A, base 35B.

*Peduncles.*—Primary peduncle (from base to the tip of the inflorescence); average of 23.1 cm in length and 2 mm in diameter, moderate strength, held at a 0° angle (straight on top of flowering stem), color of both surfaces; 183A, secondary peduncles; average of 2.9 cm in length, 1 mm in diameter, moderate in strength, held at a 65° (0°=straight upright) to primary peduncle, color of both surfaces; 183A, surface is moderately glossy, rounded, densely covered with short hairs; an average of 1 mm in length and 156D in color.

*Bracts.*—1, at base of pedicels, lanceolate in shape, between 150B and 151D in color, about 4 mm in length and 1 mm in width, acute, base truncate.

*Pedicels.*—Average of 2 mm in length and 0.5 mm in width, moderate strength, color 183A, pedicel of primary flower of each spikelet straight on top of secondary pedicel, pedicels of secondary and tertiary flowers of each spikelet in an average angle of 60° (0°=straight on top of secondary peduncle), surface is moderately glossy, rounded, densely covered with short hairs; an average of 1 mm in length and 156D in color.

Reproductive organs:

*Gynoecium.*—2 pistils, pointed in shape, about 4 mm in length, and 155A in color, styles are about 3.5 mm in length and 155A in color, ovaries are 150D in color.

*Androcoecium.*—5 stamens, anthers are ovate in shape, about 0.5 mm and 160C to 160D in color, filament 3 mm in length and 155A in color, pollen is low quantity and 160D in color.

*Seed/fruit.*—No fruit or seeds detected to date.

It is claimed:

1. A new and distinct cultivar of hybrid *Heuchera* plant named 'Circus' as herein illustrated and described.

* * * * *